(12) United States Patent
Schocket

(10) Patent No.: US 8,079,972 B2
(45) Date of Patent: Dec. 20, 2011

(54) IMPLANT FOR USE IN SURGERY FOR GLAUCOMA AND A METHOD

(76) Inventor: Stanley S. Schocket, Baltimore, MD (US)

(*) Notice: Subject to any disclaimer, the term of this patent is extended or adjusted under 35 U.S.C. 154(b) by 515 days.

(21) Appl. No.: 12/274,807

(22) Filed: Nov. 20, 2008

(65) Prior Publication Data

US 2010/0125237 A1    May 20, 2010

(51) Int. Cl.
*A61M 5/00* (2006.01)
(52) U.S. Cl. .................................. 604/8; 604/294
(58) Field of Classification Search ............... 604/8–10, 604/28, 30, 46, 128, 131, 149, 280, 294; 264/173.18, 245, 1.1; 606/107–109; 623/4, 623/4.1
See application file for complete search history.

(56) References Cited

U.S. PATENT DOCUMENTS

| | | | | |
|---|---|---|---|---|
| 4,554,918 A | * | 11/1985 | White | 604/10 |
| 4,722,724 A | | 2/1988 | Schocket | 604/8 |
| 4,826,478 A | * | 5/1989 | Schocket | 604/8 |
| 5,411,473 A | * | 5/1995 | Ahmed | 604/8 |
| 6,007,510 A | * | 12/1999 | Nigam | 604/8 |
| 6,050,970 A | * | 4/2000 | Baerveldt | 604/28 |
| 6,361,526 B1 | * | 3/2002 | Reisdorf et al. | 604/265 |

OTHER PUBLICATIONS

T.C. Chen, Editor, Surgical Techniques in Ophthalmology, Glaucoma Surgery, 2008, pp. 153-152.

* cited by examiner

*Primary Examiner* — Tatyana Zalukaeva
*Assistant Examiner* — Benedict L Hanrahan
(74) *Attorney, Agent, or Firm* — Hodes, Pressin & Katz, P.A.

(57) ABSTRACT

An implant for use in surgery for glaucoma of an eye having an oval plastic piece to which a tube is attached. The oval is wrapped as a taco enclosing the tube. The oval is placed via an incision in the conjunctiva to allow the device to be placed under the lateral or the medial rectus muscle. The tube is disposed in a sceral flap in the eye. A surgical method using the device is disclosed.

9 Claims, 5 Drawing Sheets

IMPLANT FOR USE IN SURGERY FOR GLAUCOMA AND A METHOD

BACKGROUND OF THE INVENTION

1. Field of the Invention

The present invention relates to an implant used in surgery for glaucoma and a surgical procedure for use of the implant.

2. Description of Prior Art

Glaucoma is a disease of the eye which results from increased intraocular pressure and may cause blindness. There have been various surgical procedures to correct the problem. U.S. Pat. No. 4,722,724 by Schocket discloses an anterior chamber tube shunt to an encircling band around the eye which is comparatively bulky. This procedure has achieved excellent long term pressure control but the procedure is lengthy and the tube is in the anterior chamber where there is a possibility of the tube being clogged by blood or fibrous material. Tubes in the anterior chamber often migrate forward and can cause trauma to the endothelium of the cornea.

Thus, there is a need for a surgical procedure which can be performed more rapidly to reduce possible trauma to the patient, and to be less costly. Further, there is a need for a procedure which avoids some of the problems encountered by previously known procedures. In addition, there is a need for an implant which is relatively compact.

The device and procedure of the present invention was disclosed in "Surgical Techniques in Ophthamology Glaucoma Surgery" edited by Teresa C. Chen, Saunders Elsevier, Inc., pp. 143-152 (2008).

SUMMARY OF THE INVENTION

It is an object of the present invention to provide an implant which is relatively simple to prepare and to surgically implant in the eye.

A further object of the present invention is to provide an implant and a surgical technique which directs drainage from the posterior chamber.

It is still further an object of the present invention to provide and implant a surgical procedure which does not require an encircling band on the eye.

In accordance with the teachings of the present invention, there is disclosed an implant for use in surgery for glaucoma of an eye. A shunt device is formed having an oval having edges with two opposite ends. The shunt device is formed from a plastic material. A tube having a first end is connected to the shunt device near one end of the shunt device. The shunt device is folded to resemble a taco, the edges of the oval being connected to one another with the tube being disposed within the folded oval. The folded shunt device is received in an incision under the lateral or medial rectus muscle in the eye.

In further accordance with the teachings of the present invention, there is disclosed a method for treating glaucoma in an eye with a surgical implant. An oval-shaped silicone shunt device is provided which has opposite edges. One end of a silicone tube is attached to the oval. The oval is folded in the form of a taco and the edges of the oval are connected to one another, wherein the tube is enveloped by the oval. An opposite end of the tube extends outwardly from the oval, thereby forming the shunt device. An incision is made in the conjunctiva of the eye to expose either the lateral or medial rectus muscle. The shunt device is inserted in the incision. An opening is formed through the tendon of the superior rectus muscle and the opposite end of said tube is inserted in the opening. A sclera flap is formed anterior to the superior rectus muscle and an opening is made under said flap. The opposite end of said tube is introduced into said opening under said flap and said tube is directed into the posterior chamber. Said tube is secured to the sclera. If the device is placed under the lateral rectus muscle of the left eye and if the eye moves nasally, the fluid filled device is compressed by the muscle directing the fluid into orbital tissues of the eye.

These and other objects of the present invention will become apparent from a reading of the following specification taken in conjunction with the enclosed drawings.

DESCRIPTION OF THE PREFERRED EMBODIMENTS

Figure 1:
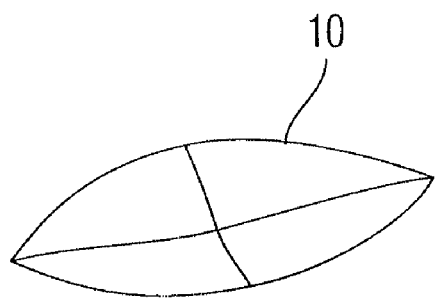
FIG. 1 is a perspective view of the template.
Figure 2:
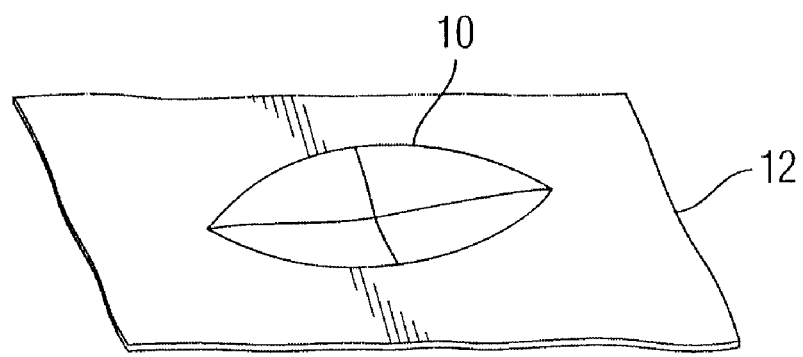
FIG. 2 is a perspective view showing the template used to cut out the shunt device from a plastic sheet.
Figure 3:
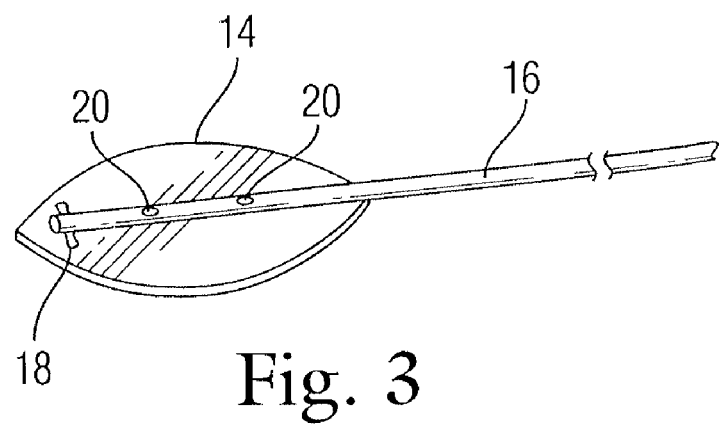
FIG. 3 is a perspective view showing the destined inferior end of the tube attached to the shunt device.
Figure 4:
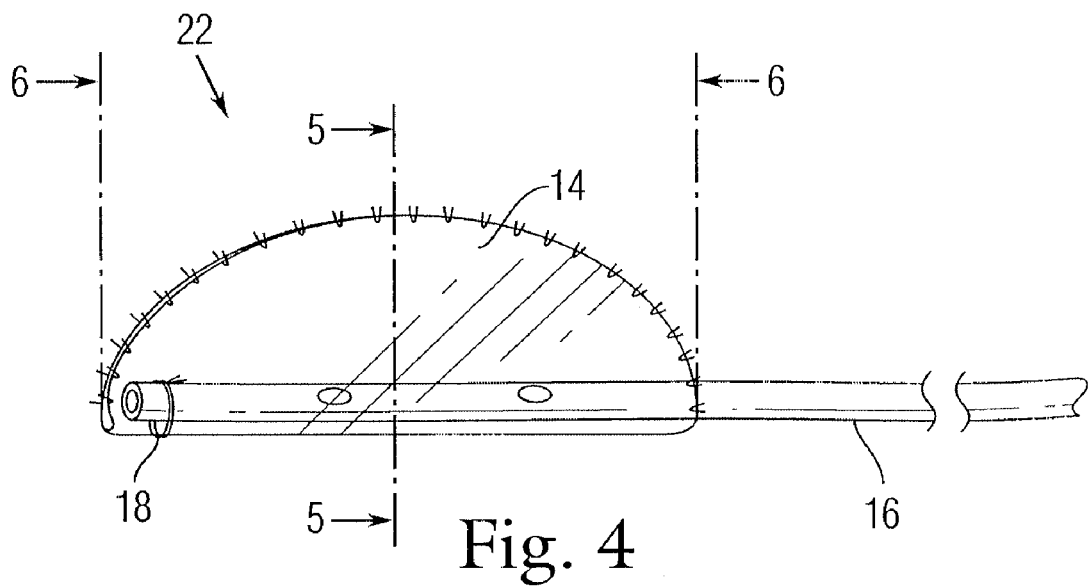
FIG. 4 is a perspective view showing the shunt device folding like a taco enveloping the tube.
Figure 5:
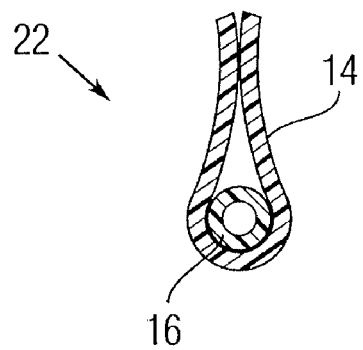
FIG. 5 is a cross-sectional view taken across the lines 5-5 of FIG. 4.
Figure 6:
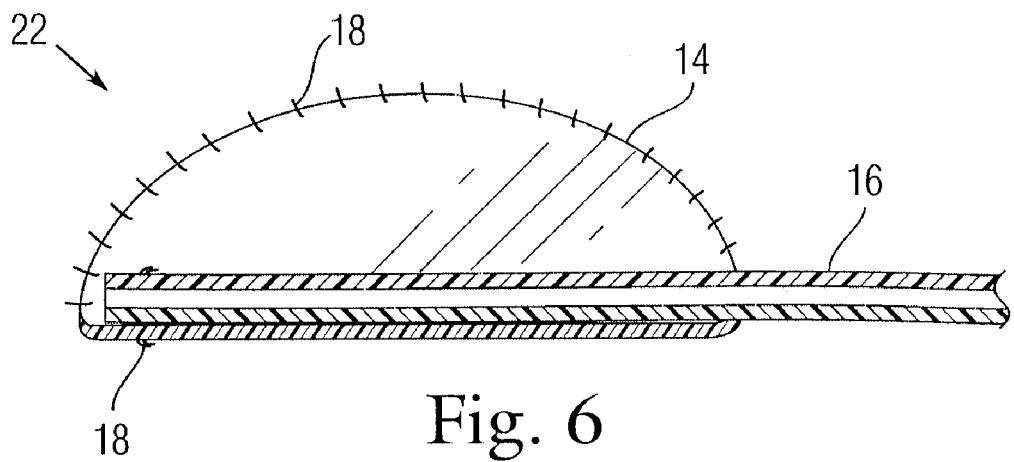
FIG. 6 is a cross-sectional view taken across the lines 6-6 of FIG. 5.

Referring to FIGS. 1-6, prior to surgery, the device is constructed in the operating room under sterile conditions. An oval template 10 is fashioned out of heavy sterile paper and measures approximately 25 mm in length and 10 mm in width. This is then superimposed on a thin silicone sheet 12, and the oval paper stencil is traced with a beaver blade forming a corresponding silicone oval 14. The tube is secured with a 7-0 Prolene 18 to the silicone sheet near the destined inferior proposed tip of the device. The tube wall is grasped with tying forceps so that two additional side exit ports 20 of 1 mm can be cut out. The oval silicone sheet is then folded like a taco, and the open edges sutured with running and intermittent locking 7-0 Prolene forming the shunt device 22.

Figure 7:
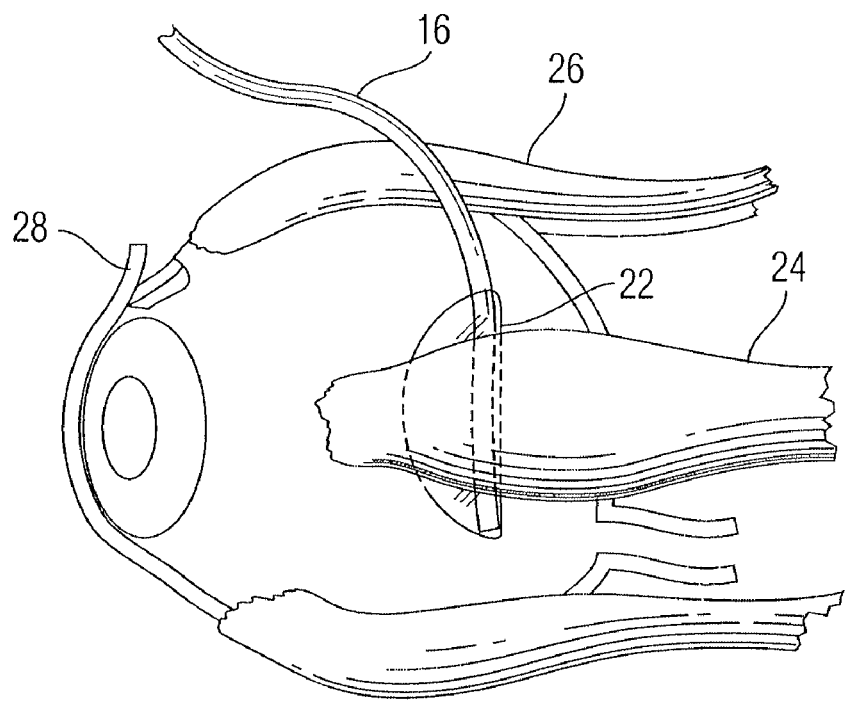
FIG. 7 is a perspective view showing the shunt device inserted in an incision under the lateral rectus muscle of the eye.

The conjunctiva is incised anterior to the superior rectus and a horizontal (medial or lateral) muscle. This is done either temporally or nasally depending on whether the device is to be placed temporally or nasally. Tenon's capsule is separated from the underlying sclera using curved scissors (Stevens). A 0 silk traction suture is then placed under the superior rectus and a 0 green suture under the lateral or medial rectus (FIG. 7).

Cotton swabs are soaked in 400 μg/cc of mitomycin C. The swabs are inserted in two quadrants between the recti muscles for 2 minutes (thin Tenons) or 4 minutes (thick Tenons). The shunt device 22 is then inserted, sutured end toward the limbus, under the horizontal rectus and is then anchored to the sclera with 7.0 Prolene, first at 10 or 2 o'clock and then inferiorly at 5 or 7 o'clock. The tip of a Colibri forceps is used to slip under the middle of the superior rectus tendon 26 anteriorly and then cauterized in order to create a 1 mm opening, the Silastic tube 16 pulled through this opening and then laid aside. A trabeculectomy type sclera flap 28, three-quarters thickness, is created with a crescent knife.

Figure 8:
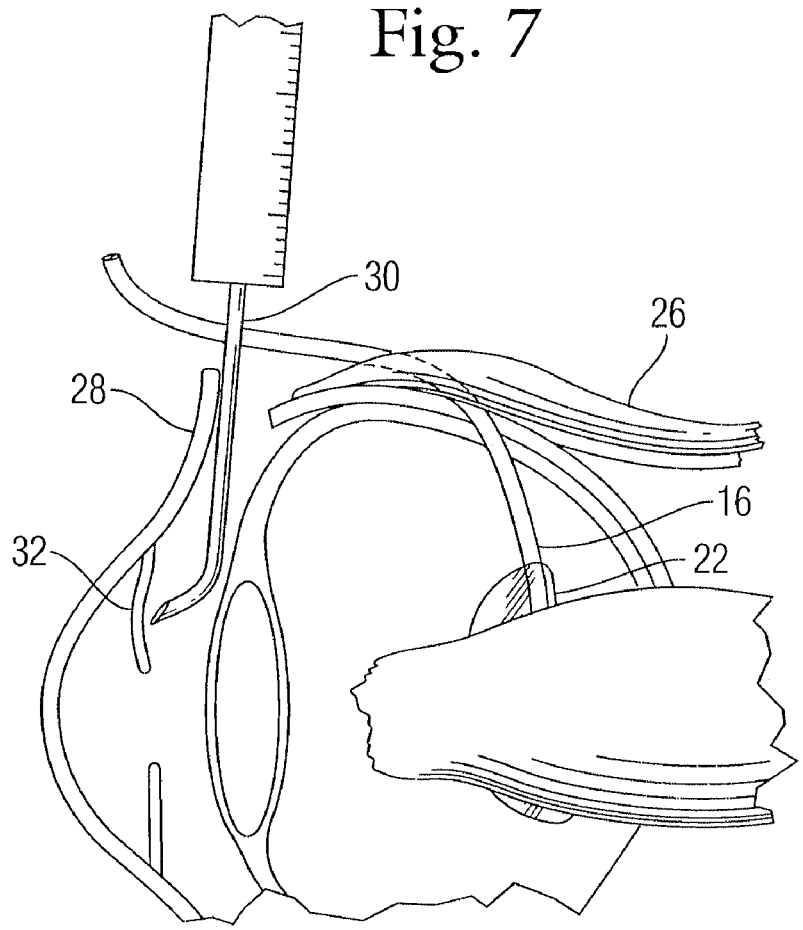
FIG. 8 is a perspective view showing a bent needle through the sclera and the iris forced upwardly toward the cornea.

A short 25 gauge needle 30 doubly bent on a 2 cc Viscoat syringe is slowly introduced into the posterior chamber through the solera 2 mm posterior to the hinge of the flap 28 (FIG. 8). The needle is gently tilted toward the iris 32 in order to identify its location. Viscoat is then injected, forcing the iris toward the cornea and thus creating a protected surgical space to introduce the tube between the posterior surface of the iris and the lens. The Silastic tube 16 is draped over the corneal limbus and cut with a Vannas scissors, allowing the bevel to face the back of the iris, and projected into the posterior chamber 3-4 mm.

Figure 9:
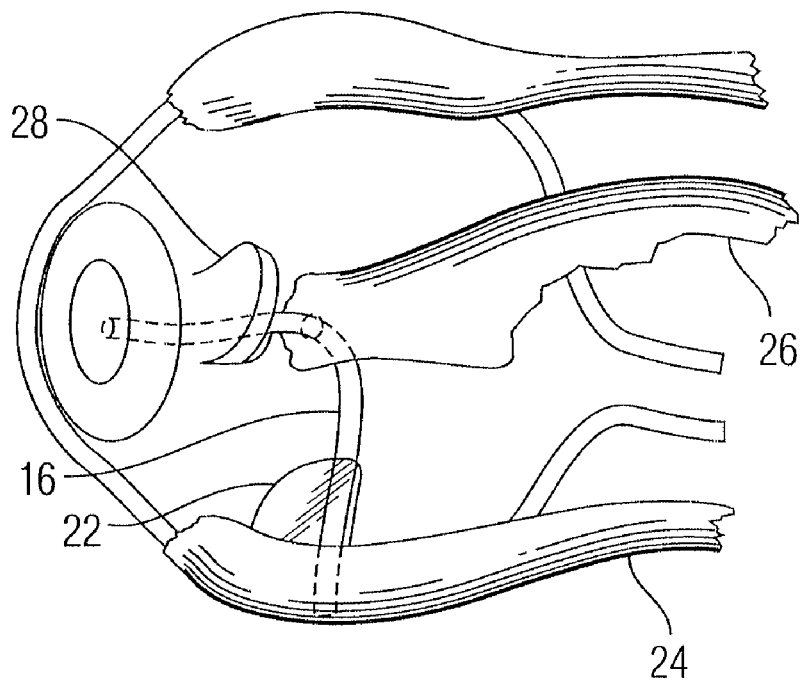
FIG. 9 is a perspective view showing the tube inserted through an opening in the tendon of the superior rectus muscle of the eye.
Figure 10:
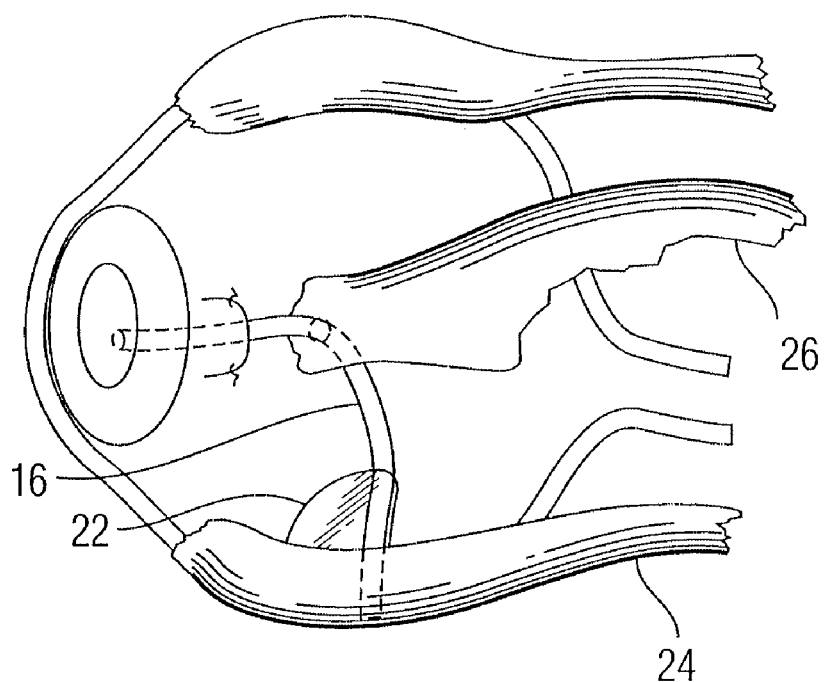
FIG. 10 is a perspective view showing the end of the tube projecting a few mm beyond the papillary rim.

The tube 16 is then introduced into the sclera opening 28 such that the tube tip extends just beyond the pupillary margin (FIG. 9). The sclera is depressed with smooth forceps just posterior to the entry site of the Silastic tube. This flattening of the sclera helps guide the tube anteriorly into the posterior chamber instead of posteriorly into the vitreous. The tube 16 is secured to the sclera with a 7-0 Prolene suture 1 mm anterior to the superior rectus tendon so that the suture is not covered by the flap. The suture is tied tight enough to flatten the tube, restricting but not blocking the outflow and to prevent tube motility. The trabeculectomy flap is then closed over the tube with two 7-0 Vicryl sutures, allowing 1-2 mm of exposed sclera bed on either side of the flap such that the flap is not compressing the tube (FIG. 10). The intraocular pressure (IOP) can be restored to normal by either injection of Viscoat, into the anterior chamber or injection of balanced salt solution into the vitreous cavity.

The conjunctiva is then closed with running locking 7-0 Vicryl. Decadron and vancomycia is injected subconjunctivally, and antibiotic solution is used to irrigate the surface of the eye.

When the eye moves, the horizontal rectus compresses the fluid filled "taco" such that fluid is pumped from the posterior chamber through the tube 16 and into the orbit of the eye. For example, if the device is placed under the lateral rectus muscle of the left eye and if the eye moves nasally, the fluid is compressed by the muscle. Thus the fluid that enters the tube and "taco" by the higher intraocular pressure is further pushed into the orbit by the compression of the muscle. This dual mechanism avoids the build-up of intraocular pressure that would otherwise occur in the glaucomatous eye. Thus, the fluid is removed from the eye avoiding the build-up of pressure which would otherwise occur.

Figure 11:
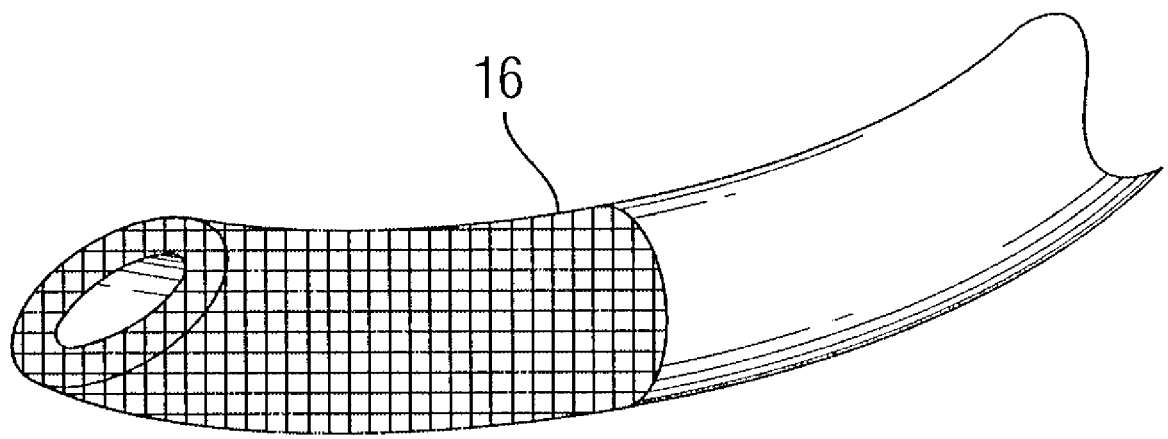
FIG. 11 is a perspective view showing the opposite end of the tube dyed a dark color.

The end of the tube 16 distal from the shunt device 22 may be dyed a dark color, such as blue or black (FIG. 11). To prevent overflow into the orbit of aqueous fluid, the lumen of tube can be restricted by a 9-0 Black Nylon which can be opened with a laser when the intraocular pressure rises. Control of fluid overflow can also be restricted by utilizing a dark dyed tube with a 50μ opening permitting a limited aqueous fluid to escape. In the event that the tube is closed or partially closed due to blood clots or other reasons, the darkened end of the tube can be targeted by a laser beam and at least one opening can be formed in the tube 16 to overcome the blockage.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. An implant for use in surgery for glaucoma of an eye, the implant comprising:
    a shunt device forming an oval having edges with two opposite ends, the shunt device being formed from a plastic material,
    a tube having a first end attached to the shunt device near one end of the shunt device, the tube extending toward the opposite end of the shunt device,
    the shunt device being folded about a center to resemble a taco, the oval edges are attached to one another by suturing, the tube being disposed within the folded oval along the center of the shunt device,
    the folded shunt device being placed under the lateral or medial rectus muscle in the eye.

2. The implant of claim 1, wherein the shunt device is formed from a single silicone sheet.

3. The implant of claim 2, wherein a template is initially formed to a desired configuration from stencil papers and traced onto the sheet of silicone to form the shunt device.

4. The implant of claim 3, wherein the template is approximately 25 mm in length and 10 mm in width.

5. The implant of claim 1, wherein the tube is formed from silicone.

6. The implant of claim 1, further having a side exit port formed on each side of the tube.

7. The implant of claim 6, wherein each side exit port is approximately 1 mm in length.

8. The implant of claim 1, wherein the first end of the tube is sutured to the shunt device.

9. The implant of claim 1, wherein the tube distal from the shunt device is dyed a dark color which can, if needed be targeted by a laser beam to form at least one opening therein.

* * * * *